(12) United States Patent
Takeyama et al.

(10) Patent No.: US 6,414,146 B1
(45) Date of Patent: Jul. 2, 2002

(54) ISOCYANURATE COMPOUND AND METHOD FOR PRODUCING THE SAME

(75) Inventors: Toshiaki Takeyama; Motohiko Hidaka, both of Funabashi; Kazuhiko Akimoto, Toyama, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/057,939

(22) Filed: Jan. 29, 2002

(30) Foreign Application Priority Data

Jan. 30, 2001 (JP) .......................... 2001-020907
Aug. 6, 2001 (JP) .......................... 2001-237387

(51) Int. Cl.$^7$ .......................................... C07D 251/34
(52) U.S. Cl. ...................................... 544/221
(58) Field of Search .......................... 544/221

(56) References Cited

FOREIGN PATENT DOCUMENTS

| EP | 0 952 155 | 10/1999 |
| EP | 1 061 080 | 12/2000 |
| JP | 11-315078 | 11/1999 |
| JP | 2000-7672 | 1/2000 |

*Primary Examiner*—John M. Ford
(74) *Attorney, Agent, or Firm*—Oblon, Spivak, McClelland, Maier & Neustadt, P.C.

(57) ABSTRACT

An isocyanurate compound of the formula (1),

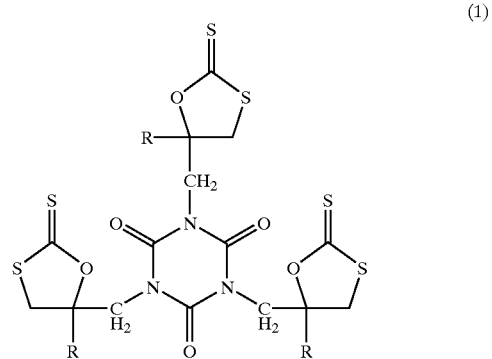

(1)

wherein R is a hydrogen atom or a methyl group, a method for producing said iscyanurate compound, characterized by reacting carbon disulfide with a triglycidyl isocyanurate compound, and a trithiol isocyanurate compound and a method for producing the same.

18 Claims, No Drawings

ISOCYANURATE COMPOUND AND METHOD FOR PRODUCING THE SAME

The present invention relates to a compound useful as a crosslinking agent for reactive molecules or reactive high polymer molecules, or an additive, and particularly the present invention relates to an isocyanurate compound having three 1,3-oxathiolane-2-thione rings in a molecule, which is suitably usable as an optical material having a high refractive index such as a plastic lens, an optical fiber or a functional film, and a starting material for a vulcanizing agent of rubber, an ink, a building sealing agent, a sealer or an adhesive agent, and also relates to a method for producing the same, and the present invention further relates to a trithiol isocyanurate compound obtained from the isocyanurate compound and a method for producing the same.

An organic high molecular material is light and easily processable, and therefore has been recently widely used as an optical material such as a plastic lens, an optical fiber or a functional film. However, as compared with an inorganic high molecular material, it has a low refractive index, which is one of important optical properties, and has a large chromatic aberration expressed by an Abbe number, and therefore it has a disadvantage that its use is limited.

On the other hand, an inorganic high molecular material has satisfactory performances in respect of heat resistance, mechanical property or chemical resistance and has a high refractive index, as compared with an organic high molecular material, but it has disadvantages that it is heavy and is not easily processable.

In the production of a conventional organic material having a high refractive index, it has been widely studied to introduce an aromatic ring, a halogen and sulfur in order to obtain a high refractive index. However, in case of introducing an aromatic ring into a structure, it is known that a double refraction is easily caused due to a high orientation property of an aromatic ring and that a transparency is degraded, and since an absorption wavelength of an aromatic ring resides relatively in the vicinity of a visible light part, an Abbe number becomes small and consequently there was a problem of providing a large chromatic aberration. This is caused by maximization of a refractive index in the vicinity of absorption wavelength, which is called as "abnormal dispersion", and this is generally well known. Accordingly, it is necessary to produce a molecule containing no aromatic ring, but there have been not so many organic materials having a high refractive index but containing no aromatic ring.

Also, an inorganic high molecular material generally has a refractive index of from 1.46 to 1.92 and an Abbe number of from 25 to 80 in a wide range, but there is not known an organic high refractive index material having a refractive index of around 1.65 and having a large Abbe number of exceeding 40. An organic high refractive index material is desired to be designed so as to provide satisfactory properties by an appropriate combination in respect of an Abbe number and a refractive index, but there is a problem that a material having wide various optical properties is not available at present. Under the circumstances, it is desired to provide an organic high refractive index material having various optical properties in respect of a refractive index and an Abbe number, and it is therefore demanded by a market to provide a novel organic high refractive index material or its starting material.

In order to satisfy the above market's demand, the present invention provides a starting material for an organic high refractive index material having a high Abbe number without degrading a transparency, and a compound useful as a curing agent or a high molecular modifier. Particularly, the present invention provides a novel isocyanurate compound having three 1,3-oxathiolane-2-thione rings in a molecule and its production method as a first invention, and also provides a trithiol isocyanurate compound obtained from the isocyanurate compound and its production method as a second invention.

As the first invention, the first embodiment resides in an isocyanurate compound of the formula (1),

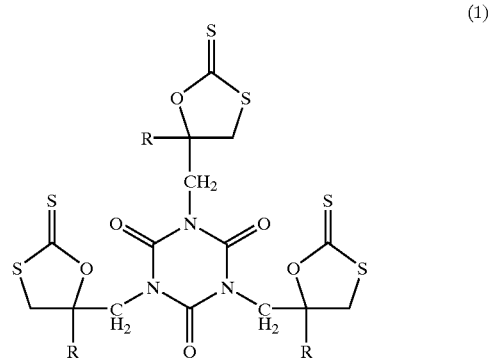

(1)

wherein R is a hydrogen atom or a methyl group.

The second embodiment resides in tris(1,3-oxathiolane-2-thion-5-ylmethyl)isocyanurate according to the first embodiment, wherein R in the formula (1) is a hydrogen atom.

The third embodiment resides in tris(5-methyl-1,3-oxathiolane-2-thion-5-ylmethyl)isocyanurate according to the first embodiment, wherein R in the formula (1) is a methyl group.

The fourth embodiment resides in a method for producing an isocyanurate compound of the formula (1),

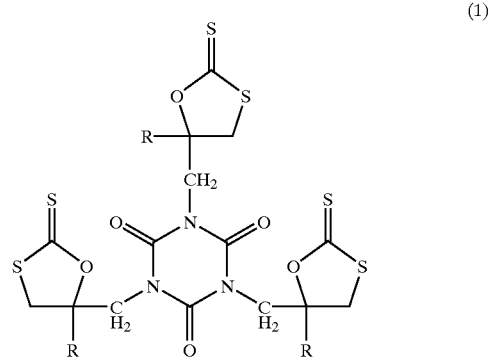

(1)

wherein R is a hydrogen atom or a methyl group, which comprises reacting carbon disulfide with a triglycidyl isocyanurate compound of the formula (2),

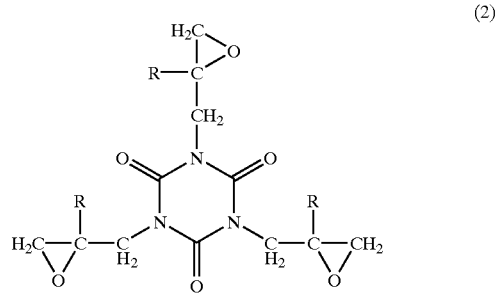

(2)

wherein R is a hydrogen atom or a methyl group.

The fifth embodiment resides in the method for producing an isocyanurate compound according to the fourth embodiment, wherein the reaction of carbon disulfide with a triglycidyl isocyanurate compound is carried out in the presence of a catalyst of at least one compound selected from the group consisting of an alkali metal halide, an alkali earth metal halide, an organic base, an alkali metal hydroxide and an onium salt.

The sixth embodiment resides in the method for producing an isocyanurate compound according to the fourth or fifth embodiment, wherein the reaction of carbon disulfide with a triglycidyl isocyanurate compound is carried out by previously mixing carbon disulfide with a catalyst of at least one compound selected from the group consisting of an alkali metal halide, an alkali earth metal halide, an organic base, an alkali metal hydroxide and an onium salt and then adding the triglycidyl isocyanurate compound thereto.

As the second invention, the seventh embodiment resides in a trithiol isocyanurate compound obtained by reacting an isocyanurate compound of the formula (1),

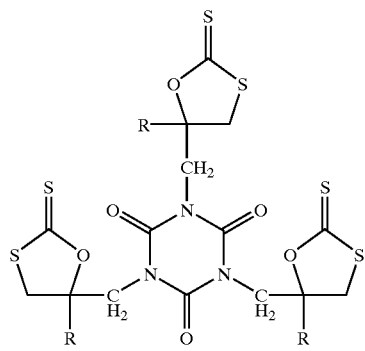

(1)

wherein R is a hydrogen atom or a methyl group, with a compound having at least one functional group selected from the group consisting of an amino group, an imino group, a hydroxyl group and a thiol group.

The eighth embodiment resides in the trithiol isocyanurate compound according to the seventh embodiment, which is obtained by reacting an isocyanurate compound with a compound having at least one amino group.

The ninth embodiment resides in the trithiol isocyanurate compound according to the seventh or eighth embodiment, which is obtained by reacting an isocyanurate compound with a primary amine having a $C_1$–$C_6$ alkyl group wherein the alkyl group may be substituted optionally with at least one different or same substituent selected from the group consisting of a $C_1$–$C_4$ alkoxy group and a $C_2$–$C_8$ dialkylamino group.

The tenth embodiment resides in the trithiol isocyanurate compound according to the seventh or eighth embodiment, which is obtained by reacting an isocyanurate compound with a benzylamine.

The eleventh embodiment resides in the trithiol isocyanurate compound according to the seventh or eighth embodiment, which is obtained by reacting an isocyanurate compound with a secondary benzylamine having a $C_1$–$C_6$ alkyl group.

The twelfth embodiment resides in the trithiol isocyanurate compound according to the seventh or eighth embodiment, which is obtained by reacting an isocyanurate compound with a primary amine having a $C_1$–$C_6$ alkenyl group.

The thirteenth embodiment resides in a method for producing a trithiol isocyanurate compound, which comprises reacting an isocyanurate compound of the formula (1),

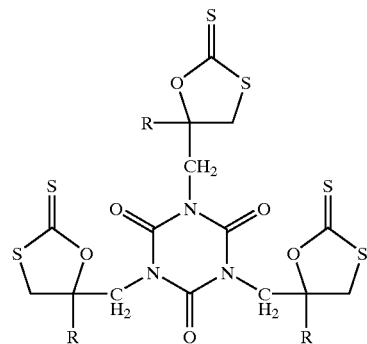

(1)

wherein R is a hydrogen atom or a methyl group, with a compound having at least one functional group selected from the group consisting of an amino group, an imino group, a hydroxyl group and a thiol group.

The fourteenth embodiment resides in the method for producing a trithiol isocyanurate compound according to the thirteenth embodiment, which comprises reacting an isocyanurate compound with a compound having at least one amino group.

The fifteenth embodiment resides in the method for producing a trithiol isocyanurate compound according to the thirteenth or fourteenth embodiment, which comprises reacting an isocyanurate compound with a primary amine having a $C_1$–$C_6$ alkyl group wherein the alkyl group may be substituted optionally with at least one different or same substituent selected from the group consisting of $C_1$–$C_4$ alkoxy group and a $C_2$–$C_8$ dialkylamino group.

The sixteenth embodiment resides in the method for producing a trithiol isocyanurate compound according to the thirteenth or fourteenth embodiment, which comprises reacting an isocyanurate compound with a benzylamine.

The seventeenth embodiment resides in the method for producing a trithiol isocyanurate compound according to the thirteenth or fourteenth embodiment, which comprises reacting an isocyanurate compound with a secondary benzylamine having a $C_1$–$C_6$ alkyl group.

The eighteenth embodiment resides in the method for producing a trithiol isocyanurate compound according to the thirteenth or fourteenth embodiment, which comprises reacting an isocyanurate compound with a primary amine having a $C_1$–$C_6$ alkenyl group.

An isocyanurate compound having three 1,3-oxathiolane-2-thione rings of the first invention is expressed by the following formula (1),

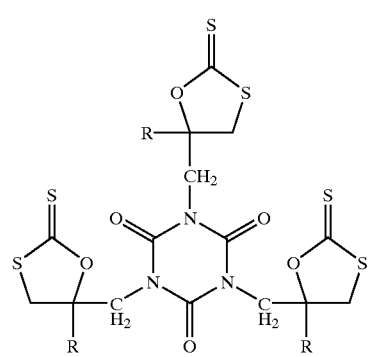

(1)

(wherein R is a hydrogen atom or a methyl group).

In the formula (1), when R is a hydrogen atom, the formula (1) expresses tris(1,3-oxathiolane-2-thion-5-ylmethyl)isocyanurate, and when R is a methyl group, the formula (1) expresses tris(5-methyl-1,3-oxathiolane-2-thion-5-ylmethyl)isocyanurate.

The production method of the first invention is fully explained in details hereinafter.

The above isocyanurate compound of the first invention is produced by reacting at least 3 mol, preferably from 3 to 10 mol, more preferably from 3 to 5 mol of carbon disulfide with one mol of a triglycidyl isocyanurate compound. The triglycidyl isocyanurate compound used herein is expressed by the following formula (2),

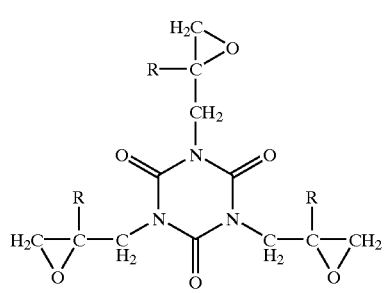

(wherein R is a hydrogen atom or a methyl group).

In the above formula (2), when R is a hydrogen atom, the formula (2) expresses tris(2,3-epoxypropyl)isocyanurate, and when R is a methyl group, the formula (2) expresses tris(2-methyl-2,3-epoxypropyl)isocyanurate.

When using a triglycidyl isocyanurate, i.e. tris(2,3-epoxypropyl)isocyanurate, as a starting material, the obtained isocyanurate compound is tris(1,3-oxathiolane-2-thion-5-ylmethyl)isocyanurate [1,3,5-tris(1,3-oxathiolane-2-thion-5-ylmethyl)-1,3,5-triazine-2,4-6-trione].

When using tris(2-methyl-2,3-epoxypropyl)isocyanurate as a starting material having a methyl group for R in the formula (2), the obtained isocyanurate compound is tris(5-methyl-1,3-oxathiolane-2-thion-5-ylmethyl)isocyanurate[1,3,5-tris(5-methyl-1,3-oxathiolane-2-thion-5-ylmethyl)-1,3,5-triazine-2,4-6 -trione].

A triglycidyl isocyanurate compound used as a starting material may be produced by any method, but tris(2,3-epoxypropyl)isocyanurate is commercially easily available as TEPIC (tradename) manufactured by Nissan Chemical Industries, Ltd. Further, by using TEPIC-S (tradename) commercially available as a high purity product and manufactured by Nissan Chemical Industries, Ltd., a side reaction can be inhibited and tris(1,3-oxathiolane-2-thion-5-ylmethyl)isocyanurate having a high purity can be obtained at a high yield.

Also, by using TEPIC-H (tradename) commercially available as a high melting point type product, tris(1,3-oxathiolane-2-thion-5-ylmethyl)isocyanurate having a high pyrolysis temperature can be preferably obtained. The TEPIC-H used as a starting material is a compound providing a highly crystalline β type crystal having a high melting point which comprises a pair of optically active substances of triglycidyl isocyanurate, i.e. (2R,2'R,2"R)-tris(2,3-epoxypropyl)isocyanurate and (2S,2'S,2"S)-tris(2,3-epoxypropyl)isocyanurate, and can be produced, for example, as described in EP 0952155 A1 (corresponding to Japanese Patent publication: JP 2000007672 A). The tris(1, 3-oxathiolane-2-thion-5-ylmethyl)isocyanurate derived from the β type tris(2,3-epoxypropyl)isocyanurate has a low solubility to various organic solvents as compared with other isomers, and provides an excellent storage stability when made into a one-pack type composition since its reaction-proceeding speed is low during storing. Thus, by using a high melting point type crystal of tris(2,3-epoxypropyl) isocyanurate, i.e. (2R,2'R,2"R)-tris(2,3-epoxypropyl) isocyanurate and (2S,2'S,2"S)-tris(2,3-epoxypropyl) isocyanurate, as a starting material, a 1:1 mixture of (1R, 1'R,1"R)-tris(1,3-oxathiolane-2-thion-5-ylmethyl) isocyanurate and (1S,1'S,1"S)-tris(1,3-oxathiolane-2-thion-5-ylmethyl)isocyanurate, having a high melting point and a low solubility, can be obtained.

Also, by using an optically active tris(2,3-epoxypropyl) isocyanurate described in EP 1061080A1 (corresponding to Japanese Patent Publication: JP 11315078 A) as a starting material, its corresponding optically active tris(1,3-oxathiolane-2-thion-5-ylmethyl)isocyanurate can be produced. For example, when using (2R,2'R,2"R)-tris(2,3-epoxypropyl)isocyanurate as a starting material, (1R,1'R, 1"R)-tris(1,3-oxathiolane-2-thion-5-ylmethyl)isocyanurate can be obtained.

Also, with regard to tris(5-methyl-1-3-oxathiolane-2-thion-5-ylmethyl)isocyanurate obtained by using tris(2-methyl-2,3-epoxypropyl)isocyanurate as a starting material, there is present the same optically active substance as described above. For example, when using (2R,2'R,2"R)-tris(2-methyl-2,3-epoxypropyl)isocyanurate as a starting material, (1R,1'R,2"R)-tris(5-methyl-1,3 -oxathiolane-2-thion-5-ylmethyl)isocyanurate can be obtained.

For carbon disulfide, 1,3-oxathiolane-2-thione or its compound can be used as a compound equivalent to carbon dioxide. In this case, carbon dioxide is generated in the system by equilibrium reaction, and it is considered to provide an aimed product by reacting the carbon disulfide with an isocyanurate compound.

In the first invention, the reaction between a triglycidyl isocyanurate compound and carbon disulfide is carried out efficiently in the presence of a catalyst of at least one compound selected from the group consisting of an alkali metal halide, an alkali earth metal halide, an organic base, an alkali metal hydroxide and an onium salt to produce an isocyanurate compound having three 1,3-oxathiolane-2-thione rings in a molecule.

Hereinafter, examples of a catalyst used in the production of an isocyanurate compound of the first invention are illustrated below.

Examples of the alkali metal halide include a lithium halide such as lithium chloride or lithium bromide, a sodium halide such as sodium chloride, sodium bromide or sodium iodide, a potassium halide such as potassium chloride, potassium bromide or potassium iodide, and the like. Examples of the alkali earth metal halide include a magnesium halide such as magnesium chloride or magnesium bromide, a calcium halide such as calcium chloride or calcium bromide, and the like. Examples of the organic base include any of generally basic organic compounds which do not participate in the reaction, for example, alkylamines such as triethylamine, diethylisopropylamine or dimethylbenzylamine, cyclic amines such as hexamethylenetetramine, pyridine, 4-dimethylaminopyridine, piperidine, piperazine, N-methylpiperidine, N,N'-dimethylpiperazine, pyridine or imidazole, and an alkali metal alkoxide such as sodium methoxide, sodium ethoxide, potassium methoxide, potassium ethoxide or potassium t-butoxide.

Examples of the alkali metal hydroxide include sodium hydroxide, potassium hydroxide or lithium hydroxide.

Examples of the onium salt include an ammonium salt, a phosphonium salt, an arsonium salt, a stibonium salt, an oxonium salt, a sulfonium salt, a selenonium salt, a stannonium salt or a iodonium salt. Also, examples of the onium salt used in the first invention include an ammonium salt, a phosphonium salt, an arsonium salt, a stibonium salt, an oxonium salt, a sulfonium salt, a selenonium salt, a stannonium salt or a iodonium salt. Examples of typical compounds include a quaternary ammonium salt such as trimethylbenzylammonium halide, triethylbenzylammonium halide, trioctylmethylammonium halide, tributylbenzylammonium halide or trimethylbenzylammonium halide. Also, examples of a quaternary phosphonium salt include a tetraalkylphosphonium halide such as tetra n-butylphosphonium halide or tetra n-propylphosphonium halide, a trialkylbenzylphosphonium halide such as triethylbenzylphosphonium halide, a triphenylmonoalkylphosphonium halide such as triphenylmethylphosphonium halide or triphenylethylphosphonium halide, a triphenylbenzylphosphonium halide, a tetraphenylphosphonium halide, a tritolylmonoarylphosphonium halide, or a tritolylmonoalkylphosphonium halide. Among the onium salts, a quaternary ammonium salt or a quaternary phosphonium salt is particularly preferable. A quaternary ammonium salt is known to form a highly basic quaternary ammonium base by being treated with wet silver oxide or sodium hydroxide or with an anion exchange resin to substitute a counter ion (such as a halogen ion) with a hydroxyl ion (OH—), but these compounds also can be used as a preferable organic base.

The catalyst may be used in a combination of two or more, and is used in a total catalyst amount of from 0.001 to 0.3 mol, preferably from 0.01 to 0.15 mol, to 1 mol of a triglycidyl isocyanurate compound.

A solvent used in the production of an isocyanurate compound of the first invention may be any solvent so long as it is inert, typical examples of which include amides such as N,N-dimethylformamide, N,N-dimethylacetamide or N-methyl-2-pyrrolidone, which is known as an aprotic polar solvent, a sulfur compound such as dimethylsulfoxide, or cyclohexanone. Examples of other solvents include aromatic hydrocarbons such as toluene or chlorobenzene, ethers such as dioxane, dimethoxyethane or tetrahydrofuran, halogenated hydrocarbons such as dichloroethane or chloroform, ketones such as acetone or methyl ethyl ketone, nitriles such as acetonitrile, nitro compounds such as nitroethane or nitrobenzene, esters such as ethyl acetate, or their mixtures. Also, other solvents such as alcohols including methanol, ethanol, isopropanol, 2-methoxyethanol or 2-ethoxyethanol, can be used, provided that they do not participate in the reaction.

The reaction using a solvent in the production of an isocyanurate compound of the first invention is carried out at a reaction temperature of from −78° C. to a boiling point of a solvent used, preferably in a range of from 0° C. to 100° C.

An isocyanurate compound of the first invention can be produced by mixing a triglycidyl isocyanurate compound, carbon disulfide, a catalyst and optionally a solvent in a reactor at the same time, but may be produced by previously placing a triglycidyl isocyanurate compound, a catalyst and optionally a solvent in a reactor and then dropwise adding carbon disulfide thereto. However, a more preferable production method comprises previously mixing carbon disulfide, at least one catalyst compound selected from the group consisting of an alkali metal halide, an alkali earth metal halide, an organic base, an alkali metal hydroxide and an onium salt, and optionally a solvent, and then adding a triglycidyl isocyanurate compound thereto. By producing an isocyanurate compound according to this method, a side reaction hardly occurs and consequently an isocyanurate compound having a high purity can be obtained.

The isocyanurate compound thus obtained in the above production method can be purified by washing, recrystallizing or reprecipitating to remove impurities including a starting material, a catalyst or a by-product. It is preferable to use a solvent for the washing step in the purification process, which has a low solubility to the isocyanurate compound product and has a power of dissolving impurities, and examples of such a preferable solvent include water, alcohols such as methanol or ethanol, ethers such as diethyl ether, tetrahydrofuran or dioxane, and the like. Also, in the purification by reprecipitation, the isocyanurate compound product is once dissolved in a polar solvent such as dimethylsulfoxide, cyclohexanone, N-methyl-2-pyrrolidone or dimethylformamide, and the resultant solution is placed in an alcohol such as methanol to precipitate a crystal which is then filtrated out, thereby removing impurities. The isocyanurate compound product purified in this manner has an improved pyrolysis temperature, and is decolored to some extent when it is colored by the reaction.

The isocyanurate compound obtained in the first invention has a large sulfur content to its molecular weight, and consequently has a high refractive index, and it is accordingly used as an additive for other materials to provide an organic material having a high refractive index. For example, the isocyanurate compound thus obtained can be mixed with a transparent resin such as acrylic resin, polyester resin or polyvinyl chloride to provide a material having a high refractive index.

The isocyanurate compound of the first invention can be preferably used not only by physically mixing with the above-mentioned resins or other monomer compounds but also by chemically reacting with other materials to provide materials excellent in adhesive properties or optical properties. This can be effected by using an active hydrogen-containing reactive compound having a reactivity to a functional group such as a 1,3-oxathiolane-2-thion-5-ylmethyl group or a 5-methyl-1,3-oxathiolane-2-thion-5-ylmethyl group in the isocyanurate compound. Preferable examples of an active hydrogen-containing functional group include an amino group, an imino group, a hydroxyl group, a thiol group and the like. When using a resin as the reactive compound, by using a resin containing at least one functional group selected from the group consisting of an amino group, an imino group, a hydroxyl group and a thiol group, the isocyanurate compound of the first invention works as a crosslinking agent to provide a material excellent in adhesive properties and optical properties. Examples of a resin used in this case include the above-mentioned transparent resins such as acrylic resin, polyester resin or polyvinyl chloride, having an amino group, an imino group, a hydroxyl group or a thiol group introduced therein.

A trithiol isocyanurate compound of the second invention is provided by reacting an active hydrogen-containing reactive compound with a functional group such as a 1,3-oxathiolane-2-thion-5-ylmethyl group or a 5-methyl-1,3-oxathiolane-2-thion-5-ylmethyl group in an isocyanurate compound of the first invention.

The above reaction may be carried out in the presence of a catalyst such as an alkali metal halide, an alkali earth metal halide, an organic base, an alkali metal hydroxide or an onium salt used in the above production of tris(1,3-oxathiolane-2-thion-5-ylmethyl)isocyanurate. Also, in case of reacting with a compound having an amino group or an imino group, by using the compound having an amino group or an imino group in an excess amount, it works as a catalyst to accelerate the reaction. These reactions may be carried out without using a solvent, but it is preferable to carry out by dispersing or dissolving the reactants in an organic solvent.

When reacting the above compound having an amino group or an imino group with tris(1,3-oxathiolane-2-thion-5-ylmethyl)isocyanurate, an addition reaction with a part or all of the tris(1,3-oxathiolane-2-thion-5-ylmethyl)isocyanurate is carried out by the above catalytic action to produce a trithiol isocyanurate compound as a thiocarbamate compound.

Examples of a trithiol isocyanurate compound obtained by reacting with a reactive compound having at least one functional group selected from the group consisting of an amino group, an imino group, a hydroxyl group and a thiol group include a compound of the following formula (3),

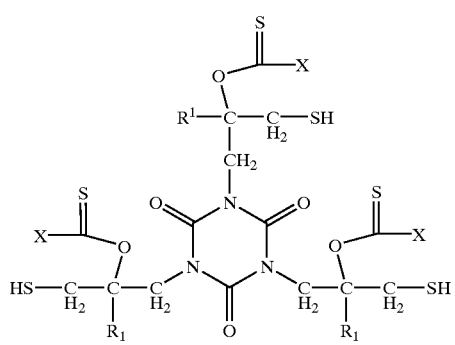

(3)

(wherein $R^1$ is a hydrogen atom or a methyl group, and X is an $NHR^2$ group, an $NR^3R^4$ group, an $OR^5$ group or an $SR^6$ group, in which $R^2$, $R^3$, $R^4$, $R^5$ and $R^6$ are respectively a hydrogen atom, a $C_1$–$C_6$ alkyl group (which may be substituted optionally with at least one different or same substituent selected from the group consisting of a $C_1$–$C_4$ alkoxy group and a $C_2$–$C_8$ dialkylamino group), a $C_1$–$C_6$ alkenyl group or a benzyl group).

Now, concrete chemical structures of the reaction products are illustrated hereinafter.

A trithiolisocyanurate compound obtained from tris(1,3-oxathiolane-2-thion-5-ylmethyl)isocyanurate and a compound having an amino group is expressed by the following formula (4).

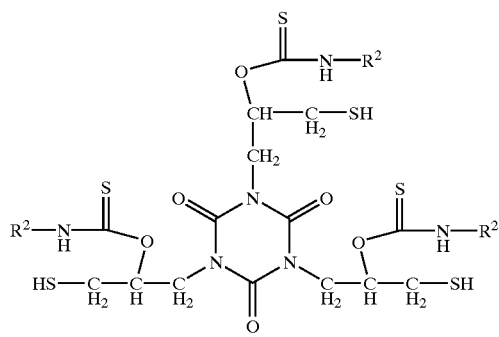

(4)

A reaction product obtained from tris(1,3-oxathiolane-2-thion-5-ylmethyl)isocyanurate and a compound having an imino group is expressed by the following formula (5).

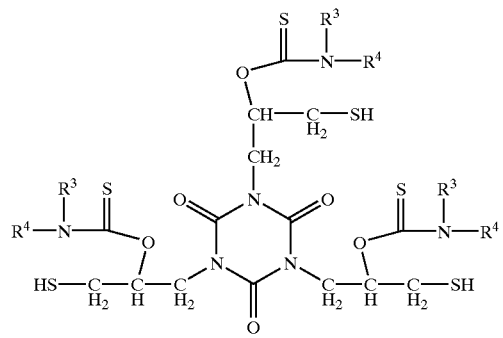

(5)

A reaction product obtained from tris(1,3-oxathiolane-2-thion-5-ylmethyl)isocyanurate and a compound having a hydroxyl group is expressed by the following formula (6).

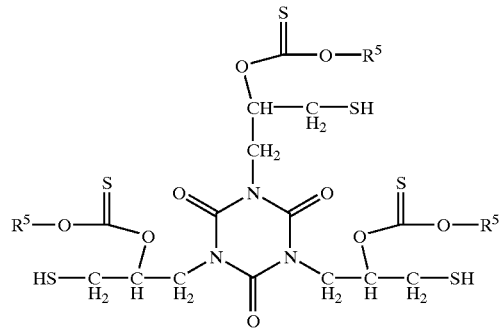

(6)

A reaction product obtained from tris(1,3-oxathiolane-2-thion-5-ylmethyl)isocyanurate and a compound having a thiol group is expressed by the following formula (7).

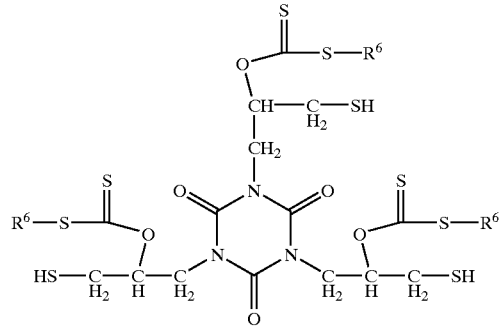

(7)

In the above formulae (4) to (7), each of $R^2$, $R^3$, $R^4$, $R^5$ and $R^6$ corresponds to that of a compound having at least one functional group selected from the group consisting of an amino group, an imino group, a hydroxyl group and a thiol group to be reacted, and when each of $R^2$, $R^3$, $R^4$, $R^5$ and $R^6$ is a methyl group, each of corresponding starting materials is methylamine in case of a compound having an amino group, dimethylamine in case of a compound having an imino group, methyl alcohol in case of a compound having a hydroxyl group and methylthiol in case of a compound having a thiol group.

A production method of the second invention is fully described in more details hereinafter.

A tris(1,3-oxathiolane-2-thion-5-ylmethyl)isocyanurate compound used as a starting material may be prepared by any method, and can be easily prepared from tris(2,3-epoxypropyl)isocyanurate (easily commercially available as TEPIC (tradename) manufactured by Nissan Chemical Industries, Ltd.) as described below. Also, it is preferable to use tris(1,3-oxathiolane-2-thion-5-ylmethyl)isocyanurate having a high purity, which is prepared from TEPIC-S (tradename) commercially available as a high purity product manufactured by Nissan Chemical Industries, Ltd. Further, it is possible to use tris(1,3-oxathiolane-2-thion-5-ylmethyl) isocyanurate prepared from TEPIC-H (tradename) commercially available as a high melting point type product. Still further, it is also possible to use optically active tris(1,3-oxathiolane-2-thion-5-ylmethyl)isocyanurate as a starting material, which is prepared from optically active tris(2,3-epoxypropyl)isocyanurate, as described in JP-A-11-315078. For example, (2R,2'R,2"R)-tris(2,3-epoxypropyl) isocyanurate produces tris(1,3-oxathiolane-2-thion-5-ylmethyl)isocyanurate having all of three asymmetric carbons composed of steric configuration of R, and a trithiol isocyanurate obtained therefrom also has all of three asymmetric carbons composed of steric configuration of R.

Examples of a compound having at least one functional group selected from the group consisting of an amino group, an imino group, a hydroxyl group and a thiol group, which is used as a reactive compound having an active hydrogen atom in the second invention, are illustrated below.

Examples of a compound having an amino group include a primary amine. Concrete examples of a primary amine having a $C_1$–$C_6$ alkyl group (which may be substituted optionally with at least one different or same substituent selected from the group consisting of a $C_1$–$C_4$ alkoxy group and a $C_2$–$C_8$ dialkylamino group) include aliphatic monoamines such as methylamine, ethylamine, butylamine, pentylamine, hexylamine, aminocyclohexane, methoxyethylamine, ethoxyethylamine, 3-methoxypropylamine, 3-ethoxypropylamine, N,N-dimethylethylenediamine, 3-(diethylamino)propylamine, 3-(dibutylamino)propylamine or the like, and examples of a primary amine having a $C_1$–$C_6$ alkenyl group include unsaturated alkylamines such as allylamine, aromatic monoamines such as aniline, benzylamine or phenethylamine, aliphatic diamines such as ethylenediamine or hexamethylenediamine, aromatic diamines such as phenylenediamine or xylylenediamine, and the like.

Examples of a compound having an imide group include a secondary amine. Concrete examples of the secondary amine include aliphatic monoamines such as dimethylamine, diethylamine, dibutylamine, dihexylamine or dicyclohexylamine, aromatic monoamines such as diphenylamine or dibenzylamine, and concrete examples of a secondary benzylamine having a $C_1$–$C_6$ alkyl group include N-methylbenzylamine, N-ethylbenzylamine, N-butylbenzylamine, N-pentylbenzylamine or N-hexylbenzylamine. Other three or more functional amines or amines substituted with a hetero ring may also be used, and for example, melamine, guanamine, imidazoles or the like may be used. Also, isocyanuric acid included in amines may be used as an active hydrogen-containing reactive compound having a reactivity to a 1,3-oxathiolane-2-thione ring.

Examples of a compound having a hydroxyl group include aliphatic monoalcohols such as methanol, ethanol, hexanol or 2-ethyl-hexanol, aromatic monoalcohols such as phenol or naphthol, glycols such as ethylene glycol, polyethylene glycol, propylene glycol, polypropylene glycol or neopentyl glycol, and examples of three or more functional compounds include glycerin, trimethylolpropane, pentaerythritol or dipentaerythritol.

Examples of a compound having a thiol group include aliphatic monothiols such as methanethiol, ethanethiol, hexanethiol or 2-ethyl-hexanethiol, aromatic monothiols such as benzenethiol or naphthalenethiol, and dithiols such as ethylenedithiol, propylenedithiol or neopentyldithiol.

Also, it is possible to use a compound having at least two or more of an amino group, an imino group, a hydroxyl group and a thiol group in combination in a molecule, examples of which include amino alcohols such as monoethanolamine or diethanolamine, and polyamines such as diethylene triamine, triethylene tetramine or hexamethylene tetramine.

The second invention is not limited to the above illustrated compounds, and these compounds may have a substituent such as a halogen or a nitro group to such an extent as not to participate in the reaction, and may have a bonding group such as ester, ether or sulfide (—S—) in a molecule.

Further, when using a compound having at least two functional groups in a molecule as a compound having at least one functional group selected from the group consisting of an amino group, an imino group, a hydroxyl group and a thiol group used in the second invention, a crosslinking reaction is caused to form a gel insoluble in a solvent. The above crosslinking reaction produces a reactive crosslinked gel having a thiol group therein, and the reactive crosslinked gel thus produced has an ability of modifying various functions by reacting with a compound reactive with the thiol group in the crosslinked gel.

In the second invention, the reaction of an isocyanurate compound with an amino group, an imino group, a hydroxyl group or a thiol group to produce a trithiol isocyanurate compound is carried out optionally in the presence of a catalyst such as a Lewis acid, an onium salt, an inorganic base, an organic base, an alkali metal hydride, an alkali metal hydroxide, an alkali metal halide, an alkali earth metal halide, an organic acid or the like.

Examples of a catalyst used in the production of a trithiol isocyanurate compound of the second invention are illustrated below.

Examples of the Lewis acid include aluminum chloride, tin chloride, titanium tetrachloride, boron trifluoride-etherate, triisopropoxy aluminum, ytterbium trifrate, and the like. Examples of the alkali metal halide include a lithium halide such as lithium chloride or lithium bromide, a sodium halide such as sodium chloride, sodium bromide or sodium iodide, a potassium halide such as potassium chloride, potassium bromide or potassium iodide, and the like.

Examples of the alkali earth metal halide include a magnesium halide such as magnesium chloride or magnesium bromide, a calcium halide such as calcium chloride or calcium bromide, and the like. The organic base may be any organic compound generally having a basic property and not participating in the reaction, examples of which include alkylamines such as triethylamine, diethylisopropylamine or dimethylbenzylamine, cyclic amines such as hexamethylenetetramine, pyridine, 4-dimethylaminopyridine, piperidine, piperazine, N-methylpiperidine, N,N'-dimethylpiperazine, pyridine or imidazole, and alkali metal alkoxides such as sodium methoxide, sodium ethoxide, potassium methoxide, potassium ethoxide or potassium t-butoxide, and the like.

Examples of the alkali metal hydroxide include sodium hydroxide, potassium hydroxide or lithium hydroxide.

Examples of the alkali metal hydride include sodium hydride or potassium hydride.

Examples of the inorganic base include potassium carbonate, cesium carbonate or potassium hydrogencarbonate.

Examples of the onium salt include an ammonium salt, a phosphonium salt, an arsonium salt, a stibonium salt, an oxonium salt, a sulfonium salt, a selenonium salt, a stannonium salt and a iodonium salt. Examples of the onium salt used in the present invention include an ammonium salt, a phosphonium salt, an arsonium salt, a stibonium salt, an oxonium salt, a sulfonium salt, a selenonium salt, a stannonium salt and a iodonium salt. Typical examples of these compounds include a quaternary ammonium salt such as trimethylbenzylammonium halide, triethylbenzylammonium halide, trioctylmethylammonium halide, tributylbenzylammonium halide or trimethylbenzylammonium halide. Also, example of a quaternary phosphonium salt include a tetraalkylphosphonium halide such as tetra n-butylphosphonium halide or tetra n-propylphosphonium halide, a trialkylbenzylphosphonium halide such as triethylbenzylphosphonium halide, a triphenylmonoalkylphosphonium halide such as triphenylmethylphosphonium halide or triphenylethylphosphonium halide, a triphenylbenzylphosphonium halide, a tetraphenylphosphonium halide, a tritolylmonoarylphosphonium halide, or a tritolylmonoalkylphosphonium halide. Among these onium salts, a quaternary ammonium salt or a quaternary phosphonium salt is particularly preferable. The quaternary ammonium salt is known to provide a strongly basic quaternary ammonium base by being treated with wet silver oxide or sodium hydroxide or an anion exchange resin to have a halogen ion as a counter ion substituted with a hydroxyl ion (OH—), and this can be used also as a preferable organic base.

The catalyst may be used in a combination of two or more, and is used in a total catalyst amount of from 0.001 to 0.3 mol, preferably from 0.01 to 0.15 mol, to 1 mol of an isocyanurate compound obtained in the first invention.

Also, when reacting with a compound having an amino group or an imino group, the compound having an amino group or an imino group is used preferably in an excess amount to accelerate the reaction. It is preferable to use the compound having an amino group or an imino group in an amount of at least 3 mol, preferably from 3 to 20 mol, more preferably from 3 to 10 mol, to 1 mol of an isocyanurate compound.

A solvent used in the production of a trithiol isocyanurate compound of the second invention may be any solvent so long as it is inert, typical examples of which include amides such as N,N-dimethylformamide, N,N-dimethylacetamide or N-methyl-2-pyrrolidone, which is known as an aprotic polar solvent, a sulfur compound such as dimethylsulfoxide, or cyclohexanone. Other examples of the solvent include aromatic hydrocarbons such as toluene or chlorobenzene, ethers such as dioxane, dimethoxyethane or tetrahydrofuran, halogenated hydrocarbons such as dichloroethane or chloroform, ketones such as acetone or methyl ethyl ketone, nitrites such as acetonitrile, nitro compounds such as nitroethane or nitrobenzene, esters such as ethyl acetate, or their mixtures. Also, a solvent such as alcohols including methanol, ethanol, isopropanol, 2-methoxyethanol or 2-ethoxyethanol may be used, provided that they do not participate in the reaction.

In the production of a trithiol isocyanurate compound of the second invention, an unpreferable coloration is sometimes caused when using ketones such as cyclohexanone, acetone or methyl ethyl ketone as a solvent among the above solvents for mixing with a compound having particularly an amino group in a molecule.

In the second invention, the reaction is carried out at a reaction temperature of from −78° C. to a boiling point of a solvent used, preferably in a range of from 0° C. to 100° C.

Further, since an oxidation reaction from the obtained thiol into disulfide also proceeds, it is preferable to carry out the reaction in an inert gas such as nitrogen or argon. A solvent may not be used for carrying out these reactions, but it is preferable to carry out the reaction by dispersing or dissolving in an organic solvent.

A trithiol isocyanurate compound of the second invention such as reaction products illustrated by the above formulae (4) to (7) easily forms a cured product having a disulfide (—S—S—) bond by oxidation polymerization due to oxygen in an oxygen atmosphere or air.

This reaction is explained below by the following chemical structural formulae. Methylamine is addition-reacted to tris(1,3-oxathiolane-2-thion-5-ylmethyl)isocyanurate to form a trithiol isocyanurate compound having the following structural formula (8),

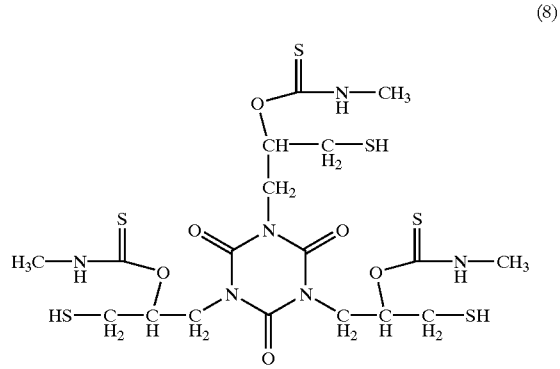

(8)

and the product thus formed is oxidized in air to form a cured product bonded by such a disulfide structure unit as illustrated by the following formula (9).

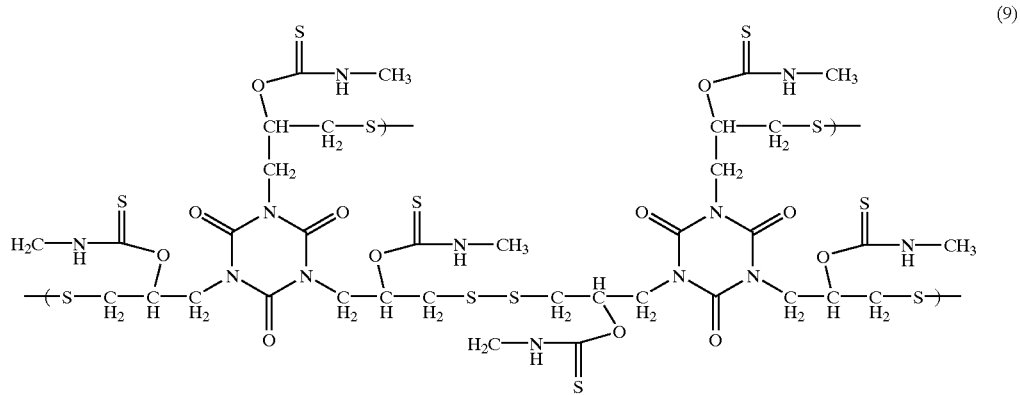

(9)

An isocyanurate compound forms a thiol in the compounds as illustrated by the above formulae (3) to (8) by reacting with the above-mentioned active hydrogen-containing reactive compound.

A solvent used in the production of a trithiol isocyanurate compound of the second invention may be any solvent, provided that it is inert, typical examples of which include amides such as N,N-dimethylformamide, N,N-dimethylacetamide or N-methyl-2-pyrrolidone, known as an aprotic polar solvent, sulfur compounds such as dimethylsulfoxide, or cyclohexanone. Examples of other solvents include aromatic hydrocarbons such as toluene or chlorobenzene, ethers such as dioxane, dimethoxyethane or tetrahydrofuran, halogenated hydrocarbons such as dichloroethane or chloroform, ketones such as acetone or methyl ethyl ketone, nitriles such as acetonitrile, nitro compounds such as nitroethane or nitrobenzene, esters such as ethyl acetate, or their mixtures. Also, a solvent such as alcohols including methanol, ethanol, isopropanol, 2-methoxyethanol or 2-ethoxyethanol, may be used, provided that it does not participate in the reaction.

In the production of a trithiol isocyanurate compound of the second invention, an unpreferable coloration is sometimes caused when using ketones such as cyclohexanone, acetone or methyl ethyl ketone among the above solvents for mixing with a compound having particularly an amino group in a molecule.

When using a solvent, the reaction of the second invention is carried out at a reaction temperature of from −78° C. to a boiling of the solvent, preferably in a range of from 0° C. to 100° C.

Also, a trithiol isocyanurate compound obtained in the second invention forms a cured product by a crosslinking reaction by mixing with a compound having at least two functional groups in a molecule, which are reactive with a thiol group in the compound. Examples of this functional group include isocyanate (—N═C═O), thioisocyanate (—N═C═S), acid anhydride, acid chloride, alkyl halide and epoxy groups. Concrete examples include isocyanates such as hexamethylene diisocyanate, toluyl diisocyanate, isophorone diisocyanate or diphenylmethane diisocyanate, acid chlorides such as terephthalic acid dichloride, alkyl halides such as xylene dichloride or xylene dibromide, glycidyl compounds such as bisphenol A diglycidyl ether, terephthalic acid diglycidyl ester or N,N-diglycidylaniline, and the like.

The crosslinking reaction of a trithiol isocyanurate compound is carried out optionally in the presence of a catalyst such as an onium salt, an inorganic base or an organic base.

Their concrete examples are illustrated below. The organic base may be any compound such as generally basic organic compounds, provided that it does not participate in the reaction, examples of which include alkylamines such as triethylamine, diethylisopropylamine or dimethylbenzylamine, cyclic amines such as hexamethylenetetramine, pyridine, 4-dimethylaminopyridine, piperidine, piperazine, N-methylpiperidine, N,N'-dimethylpiperazine, pyridine or imidazole, alkali metal alkoxides such as sodium methoxide, sodium ethoxide, potassium methoxide, potassium ethoxide or potassium t-butoxide, and the like.

Examples of the inorganic base include potassium carbonate, cesium carbonate, potassium hydrogencarbonate, and the like.

Examples of the onium salt include an ammonium salt, a phosphonium salt, an arsonium salt, a stibonium salt, an oxonium salt, a sulfonium salt, a selenonium salt, a stannonium salt, an iodonium salt, and the like. Also, examples of the onium salt used in the present invention include an ammonium salt, a phosphonium salt, an arsonium salt, a stibonium salt, an oxonium salt, a sulfonium salt, a selenonium salt, a stannonium salt, a iodonium salt, and the like. Typical examples of a quaternary ammonium salt include trimethylbenzylammonium halide, triethylbenzylammonium halide, trioctylmethylammonium halide, tributylbenzylammonium halide, trimethylbenzylanmonium halide, and the like. Also, examples of a quaternary phosphonium salt include a tetraalkylphosphonium halide such as tetra n-butylphosphonium halide or tetra n-propylphosphonium halide, a trialkylbenzylphosphonium halide such as triethylbenzylphosphonium halide, a triphenylmonoalkylphosphonium halide such as triphenylmethylphosphonium halide or triphenylethylphosphonium halide, a triphenylbenzylphosphonium halide, a tetraphenylphosphonium halide, a tritolylmonoarylphosphonium halide, or a tritolylmonoalkylphosphonium halide. Among the onium salts, a quaternary ammonium salt and a quaternary phosphonium salt are particularly preferable. The quaternary ammonium salt is known to form a strongly basic quaternary ammonium base by being treated with wet silver oxide or sodium hydroxide, or an anion exchange resin to substitute a halogen ion as a counter ion with a hydroxyl ion (OH—), and these can be used also as a preferable organic base.

The catalyst may be used in a combination of two or more, and is used in a total catalyst amount of from 0.001 to 0.3 mol, preferably from 0.01 to 0.15 mol, to 1 mol of an isocyanurate compound obtained in the first invention.

The crosslinking reaction of a trithiol isocyanurate compound is carried out preferably in the absence of a solvent, but it may be carried out in the presence of a solvent, if necessary. Examples of the solvent to be used may be any solvent, provided that it is inert to the reaction, typical examples of which include amides such as N,N-dimethylformamide, N,N-dimethylacetamide or N-methyl-2-pyrrolidone, known as an aprotic polar solvent, sulfur compounds such as dimethylsulfoxide, aromatic hydrocarbons such as toluene or chlorobenzene, ethers such as dioxane, dimethoxyethane or tetrahydrofuran, halogenated hydrocarbons such as dichloroethane or chloroform, ketones such as acetone, methyl ethyl ketone or cyclohexanone, nitrites such as acetonitrile, nitro compounds such as nitroethane or nitrobenzene, esters such as ethyl acetate, or their mixtures. Also, solvents such as alcohols including methanol, ethanol, isopropanol, 2-methoxyethanol or 2-ethoxyethanol, and amines including triethylamine or pyridine, may be used, provided that they do not participate in the reaction.

As mentioned above, an isocyanurate compound of the first invention or a trithiol isocyanurate compound of the second invention is characterized by providing a material having a high refractive index due to a high sulfur content to a molecular weight of the compound itself when it is used as a composition or as a curing agent or an additive. Further, the isocyanurate compound alone can be polymerized in the presence of a basic material as a catalyst.

Further, the isocyanurate compound of the first invention or the trithiol isocyanurate compound of the second invention does not have a benzene ring in its structure, and consequently less absorbs ultraviolet light in a long wavelength zone so that it can be used as a starting material for providing an excellent optical material having a relatively large Abbe number and a small chromatic aberration. Further, when it is used as a curing agent, it provides a tri-dimensional crosslinked structure excellent in isotropy, and consequently its double refraction is small, thus providing an excellent transparency.

Still further, tris(1,3-oxathiolane-2-thion-5-ylmethyl) isocyanurate is characterized by having a relatively low solubility to a solvent, and consequently it is possible to provide a one-pack type reactive mixture liquid together with a high molecular compound having a reactive substituent, which can be stored for a long time. Particularly, tris(1,3-oxathiolane-2-thion-5-ylmethyl)isocyanurate obtained from TEPIC-H (tradename: β type tris(2,3-epoxypropyl)-isocyanurate) manufactured by Nissan Chemical Industries, Ltd. is characterized by its low solubility to a solvent as compared with other isomers.

EXAMPLES

Hereinafter, the present invention is further illustrated with reference to Examples, but should not be limited thereto. Also, analysis processes employed in the Examples are explained below.

[Mass Spectrometric Analysis Method (MASS)]

A method employed in the Examples was an FD method (field desorption method). An FD method apparatus employed was SX-102 manufactured by JEOL Ltd.

[Proton Nuclear Magnetic Resonance Method ($^1$H-NMR)]

An identification method of reaction products in the Examples employed INOVA400 manufactured by Varian, Inc. as a $^1$H-NMR apparatus, deuterated dimethylsulfoxide or deuterated chloroform as a measuring solvent, and tetramethylsilane as a standard material.

[Melting-point Measurement, Thermal Analysis Conditions]

A melting point measuring method in each of the Examples employed TG/DTA320U manufactured by Seiko Instruments Inc., as a thermal analysis apparatus, and an endothermic temperature was defined as a melting point.

[Tg Measuring Conditions]

A Tg measuring method in each of the Examples employed DSC8230 manufactured by Rigaku International Corp., as a thermal analysis apparatus.

[Purity Measuring Conditions]

Each Example was employed a liquid chromatography (HPLC) as a purity measuring condition. An apparatus employed was a liquid chromatography apparatus manufactured by JASCO Corporation and detection was carried out at UV280 nm by using a UV detector (model No. UV-1575) as a detector. A column employed was ODS-3 (4.6 mm×250 mm) manufactured by GL Sciences Inc., and the purity measurement was carried out by using an oven temperature of 40° C., acetonitrile/water=1.5:1 as an eluate, and 4-t-butyl-toluene as an internal standard material.

[Molecular Weight Measuring Conditions]

A gel permeation chromatography (GPC) was employed for the molecular weight measuring conditions in each Example. An apparatus employed was SSC-7200 manufactured by Senshu Scientific Co., Ltd. and calculation was carried out in terms of polystyrene conversion. The measurement was carried out by using DMF as an eluate.

[Refractive Endex, Abbe Number Measurement]

A refractive index measurement method in Examples 9 to 10 employed DUV-VASE manufactured by J. A. Woollam Japan Corp. as a multi-incident spectroellipsometry, and a refractive index ($N_D$) was measured by 589 nm, and an Abbe number ($v_D$) was calculated in accordance with the following calculation formula.

$$v_D = (n_D - 1)/(n_F - n_C)$$

In the above calculation formula, $n_C$ represents a refraction index at 656 nm, $n_D$ represents a refraction index at 589 nm and $n_F$ represents a refraction index at 486 nm.

Example 1

Preparation of tris(1,3-oxathiolane-2-thion-5-ylmethyl)isocyanurate 10 g of tris(2,3-epoxypropyl)isocyanurate (TEPIC-S (tradename): high purity product, manufactured by Nissan Chemical Industries, Ltd.), 9.2 g of carbon disulfide, 0.43 g of lithium bromide as a catalyst and 20 ml of tetrahydrofuran as a solvent were placed in a reaction flask equipped with a thermometer and a stirrer, and the resultant mixture was stirred at room temperature for 24 hours. Thereafter, the reaction mixture was placed in water, and a precipitate was filtrated and was washed with methanol. A crystal thus obtained was dried at 50° C. under vacuum to obtain 17.4 g of a pale yellow powder-like tris(1,3-oxathiolane-2-thion-5-ylmethyl)isocyanurate. A purity measured by HPLC was 93.4%.

MASS (M$^+$): 525(C15H15N3O6S6)

$^1$H-NMR(ppm, DMSO-d$_6$):3.7~4.0(m, 6H), 4.2~4.4(m, 6H), 5.3~5.5(m, 3H)

Melting point (° C.): 196 (decomposition)

Example 2

Preparation of tris(1,3-oxathiolane-2-thion-5-ylmethyl)isocyanurate 9.2 g of carbon disulfide, 0.43 of lithium bromide as a catalyst and 20 ml of tetrahydrofuran as a solvent were placed in a reaction flask equipped with a thermometer and a stirrer, and the resultant mixture was stirred at room temperature for about 5 minutes, and 10 g of tris(2,3-epoxypropyl)isocyanurate (TEPIC-S (tradename): high purity product, manufactured by Nissan Chemical Industries, Ltd.) was then slowly added into the reaction container for at least 1 hour, and after the addition, the resultant mixture was stirred at room temperature for 24 hours. After the reaction, the reaction mixture was poured into water, and a precipitate was filtrated and was washed with methanol. A crystal thus obtained was dried at 50° C. under vacuum to obtain 17.8 g of a pale yellow powder-like tris(1,3-oxathiolane-2-thion-5-ylmethyl)isocyanurate. A purity measured by HPLC was 97.3%.

MASS (M$^+$): 525 (C15H15N3O6S6)

$^1$H-NMR(ppm, DMSO-d$_6$):3.7~4.0(m, 6H), 4.2~4.4(m, 6H), 5.3~5.5(m, 3H)

Melting point (° C.): 197 (decomposition)

Example 3

Preparation of tris(1,3-oxathiolane-2-thion-5-ylmethyl)isocyanurate 138.4 g of carbon disulfide, 6.45 g of lithium bromide as a catalyst and 300 ml of acetonitrile as a solvent were placed in a reaction flask equipped with a thermometer and a stirrer, and the resultant mixture was stirred at room temperature for about 5 minutes, and 150 g of tris(2,3-epoxypropyl) isocyanurate (TEPIC-S (tradename): high purity product, manufactured by Nissan Chemical Industries, Ltd.) was then slowly added into the reaction container for at least 5 hours, and after the addition, the resultant mixture was stirred at room temperature for 24 hours. After the reaction, the reaction mixture was poured into water, and a precipitate thus obtained was filtrated and was washed with methanol. A crystal thus obtained was dried at 50° C. under vacuum to obtain 265.1 g of a pale yellow powder-like tris(1,3- oxathiolane-2-thion-5-ylmethyl)isocyanurate. A purity measured by HPLC was 97.1%.

MASS (M$^+$): 525 (C15H15N3O6S6)

$^1$H-NMR (ppm, DMSO-d$_6$): 3.7~4.0 (m, 6H), 4.2~4.4 (m, 6H), 5.3~5.5 (m, 3H)

Melting point (° C.): 197 (decomposition)

Example 4

Preparation of tris(1,3-oxathiolane-2-thion-5-ylmethyl)isocyanurate 9.2 g of carbon disulfide, 0.21 g of lithium chloride as a catalyst and 20 ml of tetrahydrofuran as a solvent were placed in a reaction flask equipped with a thermometer and a stirrer, and the resultant mixture was stirred at room temperature for about 5 minutes, and 10 g of tris(2,3-epoxypropyl)isocyanurate (TEPIC-S (tradename): high purity product, manufactured by Nissan Chemical Industries, Ltd.) was then slowly added into the reaction container for at least 1 hour, and after the addition, the resultant mixture was stirred at room temperature for 24 hours. After finishing the reaction, the reaction mixture was poured into water, and a precipitate was filtrated and was washed with methanol. A crystal thus obtained was dried at 50° C. under vacuum to obtain 17.9 g of a pale yellow powder-like tris(1,3-oxathiolane-2-thion-5-ylmethyl)isocyanurate. A purity measured by HPLC was 98.1%.

MASS (M$^+$): 525 (C15H15N3O6S6)

$^1$H-NMR(ppm, DMSO-d$_6$): 3.7~4.0(m, 6H), 4.2~4.4(m, 6H), 5.3~5.5(m, 3H)

Melting point (° C.): 197 (decomposition)

Example 5

Preparation of tris(1,3-oxathiolane-2-thion-5-ylmethyl)isocyanurate 9.2 g of carbon disulfide, 0.43 g of lithium bromide as a catalyst and 20 ml of methyl isobutyl ketone as a solvent were placed in a reaction flask equipped with a thermometer and a stirrer, and the resultant mixture was stirred at room temperature for about 5 minutes, and 10 g of tris(2,3-epoxypropyl)isocyanurate (TEPIC-S (tradename): high purity product, manufactured by Nissan Chemical Industries, Ltd.) was then slowly added into the reaction container for at least 1 hour, and after the addition, the resultant mixture was stirred at room temperature for 24 hours. After finishing the reaction, the reaction mixture was poured into water, and a precipitate was filtrated and was washed with methanol. A crystal thus obtained was dried at 50° C. under vacuum to obtain 17.3 g of a pale yellow powder-like tris(1,3-oxathiolane-2-thion-5-ylmethyl)isocyanurate. A purity measured by HPLC was 95.2%.

MASS (M$^+$): 525 (C15H15N3O6S6)

$^1$H-NMR(ppm, DMSO-d$_6$):3.7~4.0(m, 6H), 4.22~4.4(m, 6H), 5.3~5.5(m, 3H)

Melting point (° C.): 197 (decomposition)

Example 6

Preparation of tris(5-methyl-1,3-oxathiolane-2-thion-5 -ylmethyl)isocyanurate 10 g of tris(2-methyl-2,3-epoxypropyl)isocyanurate (manufactured by Nissan Chemical Industries, Ltd.), 8.1 g of carbon disulfide, 0.38 g of lithium bromide as a catalyst and 20 ml of tetrahydrofuran as a solvent were placed in a reaction flask equipped with a thermometer and a stirrer, and the resultant mixture was stirred at room temperature for 24 hours. Thereafter, THF was distilled out from the reaction mixture at 50° C. under vacuum to obtain pale yellow tris(5-methyl-1,3-oxathiolane-2-thion-5-ylmethyl) isocyanurate.

MASS(M$^+$): 567(C18H21N3O6S6)

Example 7

Preparation of tris(5-methyl-1,3-oxathiolane-2-thion-5-ylmethyl)isocyanurate 1.13 g of carbon disulfide, 6 ml of THF and 0.1 g of NaOMe methanol solution (28%) were placed in a reaction flask equipped with a thermometer and a stirrer. The resultant mixture was stirred at room temperature for 10 minutes, and 1.4 g of 1,3,5-tris(2-methyl-2,3-epoxypropyl)isocyanurate (manufactured by Nissan Chemical Industries, Ltd.), was added thereto, and the resultant mixture was stirred at room temperature for 3 days. After finishing the reaction, 20 ml of water was added thereto, and a solid was filtrated out and was fully washed with water, and a crystal thus obtained was dried at 50° C. under vacuum to obtain 2.3 g of a pale yellow solid of tris(5-methyl-1,3-oxathiolane-2-thion-5-ylmethyl)isocyanurate.

MASS (M$^+$): 567 (C18H21N3O6S6)

$^1$H-NMR (ppm, DMSO-d$_6$): 1.6(s,9H), 3.7~4.0(m, 6H), 4.2~4.4 (m, 6H)

Example 8

Preparation of High Melting Point Type tris(1,3-oxathiolane-2-thion-5-ylmethyl)isocyanurate (1:1 Mixture of (1R,1'R,1"R)-tris(1,3-oxathiolane-2-thion-5-ylmethyl)isocyanurate and (1S,1'S,1"S)-tris(1,3-oxathiolane-2-thion-5-ylmethyl)isocyanurate)

10 g of high melting point type tris(2,3-epoxypropyl)isocyanurate (TEPIC-H (tradename): high purity product, manufactured by Nissan Chemical Industries, Ltd.), 9.2 g of carbon disulfide, 0.43 g of lithium bromide as a catalyst and 20 ml of tetrahydrofuran as a solvent were placed in a reaction flask equipped with a thermometer and a stirrer, and the resultant mixture was stirred at room temperature for 24 hours. Thereafter, the reaction mixture was poured into methanol, and a precipitate was filtrated and was washed with methanol. A crystal thus obtained was dried at 50° C. under vacuum to obtain 17.2 g of a pale yellow powder of tris(1,3-oxathiolane-2-thion-5-ylmethyl)isocyanurate. A purity measured by HPLC was 91.4%.

MASS(M$^+$): 525(C15H15N3O6S6)

Melting point (° C.): 223 (decomposition)

Example 9

Synthesis of Trithiol Isocyanurate Compound (Methylamine Adduct of tris(1,3-oxathiolane-2-thion-5-ylmethyl)isocyanurate) and Synthesis of Polydisulfide Film of Oxidized Cured Material 1 g of tris(1,3-oxathiolane-2-thion-5-ylmethyl) isocyanurate obtained in Example 1 was suspended in 10 g of N-methyl-2-pyrrolidone, and 2 g of 40% methylamine-methanol solution was added thereto, and the mixture was stirred at room temperature for 30 minutes. The resultant reaction product was identified by mass spectrum, and it was recognized that methylamine 3 mol adduct of tris(1,3-oxathiolane-2-thion-5-ylmethyl)isocyanurate of 618 (C18H30N6O6S6, M$^+$) was formed.

Thereafter, the colorless transparent reaction solution thus obtained was filtrated by 0.2 μm diameter filter, and was spin-coated on a 4 inch silicon wafer at 2,500 rounds per minute for 1 minute, and was then heat-cured on a hot plate at 120° C. for 5 minutes. The cured product thus obtained was analyzed by IR spectrum, and it was recognized judging from disappearance of S—H stretching vibration in the vicinity of 2,600–2,550 cm$^{-1}$ and C=S stretching vibration based on thiocarbamate in the vicinity of 1,560 cm$^{-1}$ that a polydisulfide film of an oxidized cured material or trithiol isocyanurate compound was formed. The film thus obtained had a film thickness of about 800 Å, a refraction index ($n_D$) of 1.62 and an Abbe number ($v_D$) of 33.

Example 10

Synthesis of Trithiol Isocyanurate Compound (Methylamine Adduct of High Melting Point Type tris(1,3-oxathiolane-2-thion-5-ylmethyl)isocyanurate) and Synthesis of Polydisulfide Film of Oxidized Cured Material The same procedure as in Example 9 was repeated, except that the high melting point type tris(1,3-oxathiolane-2-thion-5-ylmethyl)isocyanurate compound obtained in Example 8 was used as tris(1,3-oxathiolane-2-thion-5-ylmethyl)isocyanurate starting material. The resultant reaction product was analyzed by mass spectrum, and it was recognized that methylamine 3 mol adduct of high melting point type tris(1,3-oxathiolane-2-thion-5-ylmethyl)isocyanurate of 618 (C18H30N6O6S6,M$^+$) was formed. Thereafter, in the same manner as in Example 9, a polydisulfide film was synthesized, and its physical properties were measured. The film thus obtained had a film thickness of about 800 Å, a refraction index ($n_D$) of 1.63 and an Abbe number of ($v_D$) of 24.

Example 11

Synthesis of Trithiol Isocyanurate Compound by tris(1,3-oxathiolane-2-thion-5-ylmethyl)isocyanurate and butylamine 1 g of the tris(1,3-oxathiolane-2-thion-5-ylmethyl)isocyanurate obtained in Example 1 was suspended in 10 g of tetrahydrofuran, and 0.5 g of butylamine was added thereto, and the resultant mixture was stirred at room temperature for 1 night in a nitrogen atmosphere. After finishing the reaction, the solvent was distilled off to obtain 1.45 g of a colorless foam-like compound.

MASS (M$^+$): 744 (C27H48N6O6S6)

$^1$H-NMR (ppm, CDCl$_3$): 0.8~1.0(t, 9H), 1.3~1.7(m, 12H), 1.86(bs, 3H), 2.7~3.0(m, 6H), 3.0~3.6(m, 6H), 4.0~4.5(m, 6H), 5.5~6.1(m, 3H), 6.8~7.1(m, 3H)

Example 12

Synthesis of Trithiol Isocyanurate Compound by tris(1,3-oxathiolane-2-thion-5-ylmethyl)isocyanurate and benzylamine 5.26 g of the tris(1,3-oxathiolane-2-thion-5-ylmethyl)isocyanurate obtained in Example 1 was suspended in 10 ml of tetrahydrofuran, and 3.85 g of benzylamine was added thereto, and the resultant mixture was stirred at room temperature for 1 night in a nitrogen atmosphere. After finishing the reaction, the solvent was distilled off to obtain 8.95 g of a colorless foam-like compound.

MASS (M$^+$): 846 (C36H42N6O6S6).

$^1$H-NMR (ppm, CDCl$_3$): 1.71 (bs, 3H), 2.6~2.9 (m, 6H), 3.9~4.9 (m, 12H), 5.6~5.9 (m, 3H), 7.2~7.6 (m, 18H)

Example 13

Synthesis of Trithiol Isocyanurate Compound by tris(1,3-oxathiolane-2-thion-5-ylmethyl)isocyanurate and N-methylbenzylamine 2.63 g of the tris(1,3-oxathiolane-2-thion-5-ylmethyl)isocyanurate obtained in Example 1 was suspended in 5 ml of tetrahydrofuran, and 1.84 g of N-methylbenzylamine was added thereto, and the resultant mixture was stirred at room temperature for 1 night in a nitrogen atmosphere. After finishing the reaction, the solvent was distilled off to obtain 4.5 g of a pale yellow foam-like compound.

MASS (M$^+$): 888 (C39H48N6O6S6)

$^1$H-NMR (ppm, CDCl$_3$): 1.62 (b s, 3H) 2.7~3.4 (m, 15H) 3.8~4.5 (m, 6H) 4.5~5.2 (m, 6H) 5.7~6.1 (m, 3H) 7.1~7.5 (m, 15H)

Example 14

Synthesis of Trithiol Isocyanurate Compound by tris(1,3-oxathiolane-2-thion-5-ylmethyl)isocyanurate and allylamine 2.1 g of the tris(1,3-oxathiolane-2-thion-5-ylmethyl)isocyanurate obtained in Example 1 was suspended in 5 ml of tetrahydrofuran, and 0.77 g of allylamine was added thereto, and the resultant mixture was stirred at room temperature for 1 night in a nitrogen atmosphere. After finishing the reaction, the solvent was distilled off to obtain 2.78 g of a colorless foam-like compound.

MASS (M$^+$): 696 (C24H36N6O6S6)

$^1$H-NMR (ppm, CDCl$_3$): 1.65(bs, 3H), 2.7~3.1(m, 6H), 3.7~4.6(m, 12H), 5.1~5.4(m, 6H), 5.6~6.1(m, 6H), 6.6~7.4 (m, 3H)

Example 15

Synthesis of Trithiol Isocyanurate Derivative by tris(1,3-oxathiolane-2-thion-5-ylmethyl)isocyanurate and 2-ethoxyethylamine 1.05 g of the tris(1,3-oxathiolane-2-thion-5-ylmethyl)isocyanurate obtained in Example 1 was suspended in 5 ml of tetrahydrofuran, and 0.56 g of 2-ethoxyethylamine was added thereto, and the resultant mixture was stirred at room temperature for 1 night in a nitrogen atmosphere. After finishing the reaction, the solvent was distilled off to obtain 1.56 g of a pale yellow highly viscous compound.

MASS (M$^+$): 792 (C27H48N6O9S6)

$^1$H-NMR (ppm, CDCl$_3$): 1.20 (t, 9H), 1.79 (b s, 3H), 2.7~3.0 (m, 6H), 3.4~3.9 (m, 18H), 4.0~4.5 (m, 6H), 5.6~6.1 (m, 3H), 6.9~7.6 (m, 3H)

Example 16

Synthesis of Trithiol Isocyanurate Derivative by tris(1,3-oxathiolane-2-thion-5-ylmethyl)isocyanurate and N,N-dimethylethylenediamine 1.05 g of the tris(1,3-oxathiolane-2-thion-5-ylmethyl)isocyanurate obtained in Example 1 was suspended in 5 ml of tetrahydrofuran, and 0.56 g of N,N-dimethylethylenediamine was added thereto, and the resultant mixture was stirred at room temperature for 1 night in a nitrogen atmosphere. After finishing the reaction, the solvent was distilled off to obtain 1.56 g of a colorless foam-like compound.

MASS ($M^{30}$): 789 ($C_{27}H_{51}N_9O_6S_6$)

$^1$H-NMR (ppm, $CDCl_3$): 1.86 (b s, 3H), 2.1~2.6 (m, 24H), 2.7~3.1 (m, 6H), 3.1~3.9 (m, 6H), 3.9~4.6 (m, 6H), 5.7~6.1 (m, 3H), 7.7~8.4 (m, 3H)

Application Example 1

Acetylation of Benzylamine Adduct of tris(1,3-oxathiolane-2-thion-5-ylmethyl)isocyanurate 1.6 g of the tris(1,3-oxathiolane-2-thion-5-ylmethyl)isocyanurate-benzylamine 3 mol adduct obtained in Example 12 was suspended in 10 ml of tetrahydrofuran, and 0.5 g of acetic anhydride and 0.5 g of pyridine were dropwise added thereto, and the resultant mixture was stirred at room temperature for 1 night in a nitrogen atmosphere. After finishing the reaction, the solvent was distilled off, and solvent extraction with water and chloroform and concentration were carried out to obtain 2.64 g of a crude product. The crude product thus obtained was subjected to column (solvent:chloroform)-purification to obtain 1.73 g of a colorless foam-like aimed product.

MASS ($M^+$): 972 ($C_{42}H_{48}N_6O_9S_6$)

$^1$H-NMR (ppm, $CDCl_3$): 1.65 (b s, 3H), 2.2~2.4 (m, 9H), 3.0~3.5(m, 6H), 3.8~4.9 (m, 12H), 5.6~6.1 (m, 3H), 7.2~7.4 (m, 15H)

Application Example 2

Benzylation of Benzylamine Adduct of tris(1,3-oxathiolane-2-thion-5-ylmethyl)isocyanurate 1.55 g of the tris(1,3-oxathiolane-2-thion-5-ylmethyl)isocyanurate-benzylamine 3 mol adduct obtained in Example 12 was suspended in 15 ml of tetrahydrofuran, and 0.96 g of benzyl bromide and 1 ml of triethylamine were dropwise added thereto, and the resultant mixture was stirred at room temperature for 1 night in a nitrogen atmosphere. After finishing the reaction, an undissolved material was removed, and the reaction mixture was concentrated to obtain 2.0 g of a crude product. The crude product thus obtained was subjected to column (solvent:chloroform)-purification to obtain 1.4 g of a colorless foam-like aimed product.

MASS ($M^+$): 972 ($C_{42}H_{48}N_6O_9S_6$)

$^1$H-NMR (ppm, $CDCl_3$): 2.5~2.9 (m, 6H), 3.6~3.9 (m, 6H), 3.9~4.8 (m, 12H), 5.7~6.1 (m, 3H), 7.1~7.6 (m, 33H)

Application Example 3

Benzoylation of benzylamine Adduct of tris(1,3-oxathiolane-2-thion-5-ylmethyl)isocyanurate 0.86 g of the tris(1,3-oxathiolane-2-thion-5-ylmethyl)isocyanurate-benzylamine 3 mol adduct obtained in Example 12 was suspended in 5 ml of tetrahydrofuran, and 0.42 g of benzoyl chloride and 0.6 ml of triethylamine were dropwise added thereto, and the resultant mixture was stirred at room temperature for 1 night in a nitrogen atmosphere. After finishing the reaction, an undissolved material was removed, and a crude product obtained by concentration was subjected to column (solvent:chloroform)-purification to obtain 1.1 g of a colorless foam-like aimed product.

MASS ($M^{30}$): 1158 ($C_{57}H_{54}N_6O_9S_6$)

$^1$H-NMR (ppm, $CDCl_3$): 3.2~3.7 (m, 6H), 3.8~4.9 (m, 12H), 5.8~6.1 (m, 3H), 7.1~7.7 (m, 27H), 7.7~8.1 (m, 6H)

Application Example 4

Reaction of tris(1,3-oxathiolane-2-thion-5-ylmethyl) isocyanurate-benzylamine 3 mol Adduct and phenyl isocyanate 1.6 g of the tris(1,3-oxathiolane-2-thion-5-ylmethyl)isocyanurate-benzylamine 3 mol adduct obtained in Example 12 was suspended in 5 ml of tetrahydrofuran, and 0.68 g of phenyl isocyanate was added thereto, and the resultant mixture was stirred at room temperature for 1 night in a nitrogen atmosphere. After finishing the reaction, the solvent was concentrated to obtain 2.48 g of a crude product. The crude product thus obtained was subjected to column (solvent: chloroform)-purification to obtain 1.93 g of a colorless foam-like aimed product.

MASS ($M^{30}$): 1203 ($C_{57}H_{57}N_9O_9S_6$)

$^1$H-NMR (ppm, $CDCl_3$): 3.1~3.5 (m, 6H), 3.9~4.8 (m, 12H), 5.8~6.1 (m, 3H), 7.0~7.6 (m, 36H)

Application Example 5

Reaction of tris(1,3-oxathiolane-2-thion-5-ylmethyl) isocyanurate-benzylamine 3 Adduct and hexamethylene diisocyanate 1.7 g of the tris(1,3-oxathiolane-2-thion-5-ylmethyl)isocyanurate-benzylamine 3 mol adduct obtained in Example 12 was suspended in 8 ml of tetrahydrofuran, and 0.5 g of hexamethylene diisocyanate was added thereto, and the resultant mixture was stirred at room temperature for 1 night in a nitrogen atmosphere. After finishing the reaction, the reaction mixture was poured into 50 ml of acetonitrile to carry out reprecipitation, and the precipitated material was dried to obtain 2.0 g of a white solid.

Tg: 60° C., decomposition-initiation temperature: 203° C. (reduction of 5 wt %)

Number average molecular weight (Mn): 2200

Weight average molecular weight (Mw): 5900

Polydispersity (Mw/Mn): 2.66

According to the present invention, an isocyanurate compound having three 1,3-oxathiolane-2-thione rings in a molecular could be obtained, and a method for producing this isocyanurate compound was discovered.

The isocyanurate compound having three 1,3-oxathiolane-2-thione rings in a molecule itself can be used as an additive to other material system to obtain an organic material having a high refractive index. Also, the isocyanurate compound of the present invention can be used as a crosslinking agent for polyamine, polyol, polythiol or the like, which is a reactive compound containing active hydrogen reactive with a 1,3-oxathiolane-2-thion-5-ylmethyl group or a 5-methyl-1,3-oxathiolane-2-thion-5-ylmethyl group which is a substituent site of the isocyanurate compound, and in this case also, an organic material having a high refractive index can be obtained. Further, not only by using the properties of this compound itself but also by using this compound as a curing agent or an additive, a material having a high refractive index can be provided since this compound has a large sulfur content to its molecular weight.

The isocyanurate compound of the first invention provides a trithiol isocyanurate compound by reacting with a compound having at least one functional group selected from the group consisting of a primary amine, a secondary amine, a hydroxyl group and a thiol group. The trithiol isocyanurate compound of the second invention is a compound having a thiol group in a side chain, and this compound can be used as a curing agent for a polyepoxy compound or a polyisocyanate compound. Also, when the trithiol isocyanurate compound is subjected to oxidation polymerization by oxygen, a cured film having a polydisulfide structure can be obtained. It has been discovered that this cured product provides an optically excellent material having a relatively high refractive index and a satisfactory Abbe number.

On the other hand, it is possible to polymerize the isocyanurate compound alone in the presence of a catalyst of a basic material.

The entire disclosures of Japanese Patent Application No. 2001-020907 filed on Jan. 30, 2001 and Japanese Patent Application No. 2001-237387 filed on Aug. 6, 2001 including specifications, claims and summaries are incorporated herein by reference in their entireties.

What is claimed is:

1. An isocyanurate compound of the formula (1),

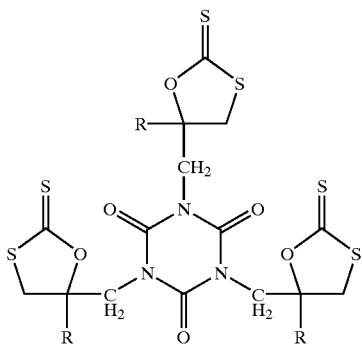

wherein R is a hydrogen atom or a methyl group.

2. Tris(1,3-oxathiolane-2-thion-5-ylmethyl)isocyanurate according to claim 1, wherein R in the formula (1) is a hydrogen atom.

3. Tris(5-methyl-1,3-oxathiolane-2-thion-5-ylmethyl)isocyanurate according to claim 1, wherein R in the formula (1) is a methyl group.

4. A method for producing an isocyanurate compound of the formula (1),

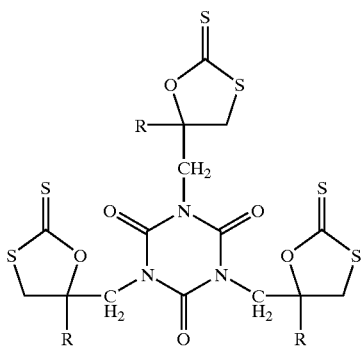

wherein R is a hydrogen atom or a methyl group, which comprises reacting carbon disulfide with a triglycidyl isocyanurate compound of the formula (2),

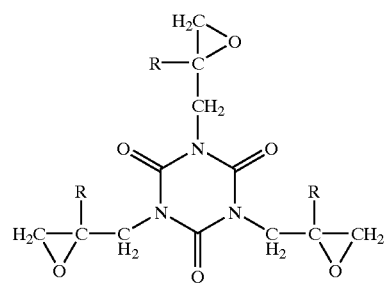

wherein R is a hydrogen atom or a methyl group.

5. The method for producing an isocyanurate compound according to claim 4, wherein the reaction of carbon disulfide with a triglycidyl isocyanurate compound is carried out in the presence of a catalyst of at least one compound selected from the group consisting of an alkali metal halide, an alkali earth metal halide, an organic base, an alkali metal hydroxide and an onium salt.

6. The method for producing an isocyanurate compound according to claim 4, wherein the reaction of carbon disulfide with a triglycidyl isocyanurate compound is carried out by previously mixing carbon disulfide with a catalyst of at least one compound selected from the group consisting of an alkali metal halide, an alkali earth metal halide, an organic base, an alkali metal hydroxide and an onium salt and then adding the triglycidyl isocyanurate compound thereto.

7. A trithiol isocyanurate compound obtained by reacting an isocyanurate compound of the formula (1),

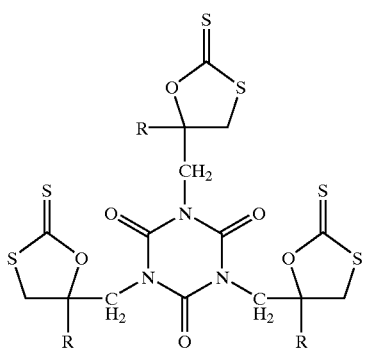

wherein R is a hydrogen atom or a methyl group, with a compound having at least one functional group selected from the group consisting of an amino group, an imino group, a hydroxyl group and a thiol group.

8. The trithiol isocyanurate compound according to claim 7, which is obtained by reacting an isocyanurate compound with a compound having at least one amino group.

9. The trithiol isocyanurate compound according to claim 7, which is obtained by reacting an isocyanurate compound with a primary amine having a $C_1$–$C_6$ alkyl group wherein the alkyl group may be substituted optionally with at least one different or same substituent selected from the group consisting of a $C_1$–$C_4$ alkoxy group and a $C_2$–$C_8$ dialkylamino group.

10. The trithiol isocyanurate compound according to claim 7, which is obtained by reacting an isocyanurate compound with a benzylamine.

11. The trithiol isocyanurate compound according to claim 7, which is obtained by reacting an isocyanurate compound with a secondary benzylamine having a $C_1$–$C_6$ alkyl group.

12. The trithiol isocyanurate compound according to claim 7, which is obtained by reacting an isocyanurate compound with a primary amine having a $C_1$–$C_6$ alkenyl group.

13. A method for producing a trithiol isocyanurate compound, which comprises reacting an isocyanurate compound of the formula (1),

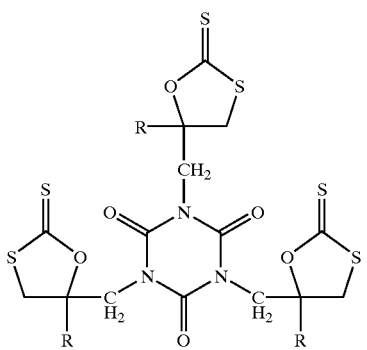

(1)

wherein R is a hydrogen atom or a methyl group, with a compound having at least one functional group selected from the group consisting of an amino group, an imino group, a hydroxyl group and a thiol group.

14. The method for producing a trithiol isocyanurate compound according to claim 13, which comprises reacting an isocyanurate compound with a compound having at least one amino group.

15. The method for producing a trithiol isocyanurate compound according to claim 13, which comprises reacting an isocyanurate compound with a primary amine having a $C_1$–$C_6$ alkyl group wherein the alkyl group may be substituted optionally with at least one different or same substituent selected from the group consisting of a $C_1$–$C_4$ alkoxy group and a $C_2$–$C_8$ dialkylamino group.

16. The method for producing a trithiol isocyanurate compound according to claim 13, which comprises reacting an isocyanurate compound with a benzylamine.

17. The method for producing a trithiol isocyanurate compound according to claim 13, which comprises reacting an isocyanurate compound with a secondary benzylamine having a $C_1$–$C_6$ alkyl group.

18. The method for producing a trithiol isocyanurate compound according to claim 13, which comprises reacting an isocyanurate compound with a primary amine having a $C_1$–$C_6$ alkenyl group.

* * * * *